(12) United States Patent
Adler

(10) Patent No.: US 6,885,000 B1
(45) Date of Patent: Apr. 26, 2005

(54) METHOD AND APPARATUS TO CORRECT FOR STAGE MOTION IN E-BEAM INSPECTION

(75) Inventor: David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/702,270

(22) Filed: Nov. 6, 2003

Related U.S. Application Data

(60) Provisional application No. 60/475,086, filed on Jun. 2, 2003.

(51) Int. Cl.[7] .......................... G01N 21/00; H01J 37/244
(52) U.S. Cl. .......................... 250/310; 250/311; 250/307
(58) Field of Search ................................ 250/310, 311, 250/307

(56) References Cited

U.S. PATENT DOCUMENTS

| | | | | |
|---|---|---|---|---|
| 4,877,326 A | | 10/1989 | Chadwick et al. | |
| 4,954,705 A | * | 9/1990 | Brunner et al. | 250/310 |
| 5,973,323 A | * | 10/1999 | Adler et al. | 250/310 |
| 6,038,018 A | * | 3/2000 | Yamazaki et al. | 356/237.1 |
| 6,365,897 B1 | * | 4/2002 | Hamashima et al. | 250/310 |
| 6,677,587 B1 | * | 1/2004 | Kohama | 250/310 |
| 6,686,591 B1 | * | 2/2004 | Ito et al. | 250/311 |
| 2002/0148975 A1 | * | 10/2002 | Kimba et al. | 250/492.1 |

* cited by examiner

Primary Examiner—Nikita Wells
Assistant Examiner—Anthony Quash
(74) Attorney, Agent, or Firm—Okamoto & Benedicto LLP

(57) ABSTRACT

One embodiment disclosed relates to an apparatus for inspecting a substrate. The apparatus includes at least an illumination system, a stage, a multiple-pixel detector, an imaging system, a deflector, and a deflector controller. The illumination system is configured to expose at least a portion of the substrate to an incident beam which causes said portion to emit radiation. The stage holds the substrate and moves the substrate relative to the beam during said exposure of the substrate. The imaging system images the emitted radiation onto the multi-pixel detector, which includes an array of detector elements configured to detect the emitted radiation. The deflector is configured to deflect the emitted radiation under control of the deflector controller. The deflection is controlled so as to compensate for the motion of the substrate relative to the beam.

19 Claims, 9 Drawing Sheets

| D1 | E1 | F1 | G1 | H1 |
|----|----|----|----|----|
| D2 | E2 | F2 | G2 | H2 |
| D3 | E3 | F3 | G3 | H3 |
| D4 | E4 | F4 | G4 | H4 |
| D5 | E5 | F5 | G5 | H5 |

FIG. 4A

| E1 | F1 | G1 | H1 | I1 |
|----|----|----|----|----|
| E2 | F2 | G2 | H2 | I2 |
| E3 | F3 | G3 | H3 | I3 |
| E4 | F4 | G4 | H4 | I4 |
| E5 | F5 | G5 | H5 | I5 |

FIG. 4B

METHOD AND APPARATUS TO CORRECT FOR STAGE MOTION IN E-BEAM INSPECTION

CROSS-REFERENCE TO RELATED APPLICATIONS

The present application claims the benefit of provisional patent application No. 60/475,086, filed Jun. 2, 2003, entitled "Method and Apparatus to Correct for Stage Motion in E-Beam Inspection", by inventor David L. Adler, the disclosure of which is hereby incorporated by reference.

BACKGROUND OF THE INVENTION

1. Field of the Invention

The present invention relates generally to automated inspection methods and apparatus in semiconductor manufacturing and the like.

2. Description of the Background Art

It is desirable to improve the quality of image data obtained during the automated inspection of manufactured substrates such as semiconductor wafers.

SUMMARY

One embodiment of the invention pertains to an apparatus for inspecting a substrate. The apparatus includes at least an illumination system, a stage, a multiple-pixel detector, an imaging system, a deflector, and a deflector controller. The illumination system is configured to expose at least a portion of the substrate to an incident beam which causes said portion to emit radiation. The stage holds the substrate and moves the substrate relative to the beam during said exposure of the substrate. The imaging system images the emitted radiation onto the multi-pixel detector, which includes an array of pixel detector elements configured to detect the emitted radiation. The deflector is configured to deflect the emitted radiation under control of the deflector controller. The deflection is controlled so as to compensate for the motion of the substrate relative to the beam.

Another embodiment of the invention pertains to a method of inspecting a substrate. At least a portion of the substrate is exposed to an incident beam, which causes said portion to emit radiation. During the exposure, the substrate is moved relative to the incident beam. The emitted radiation is deflected and imaged onto at least one detector. The deflection compensates for the relative motion and causes emitted radiation for each image pixel to accumulate at a corresponding detector element.

BRIEF DESCRIPTION OF THE DRAWINGS

FIGS. 4A and 4B are illustrations of a correspondence of image pixels to detector elements before and after a transition in accordance with an embodiment of the invention.

DETAILED DESCRIPTION

Present methods of automated inspection have various disadvantages. For example, in systems using a time delay integration (TDI) sensor, the accumulated charges corresponding to image pixels are typically moved from one row to the next in discrete increments. However, the motion of the substrate under inspection may be continuous, not discrete. This results in undesirable blur of the image because the movement of the image pixels and the transfer of charge within the TDI sensor are not precisely synchronized.

Figure 1:
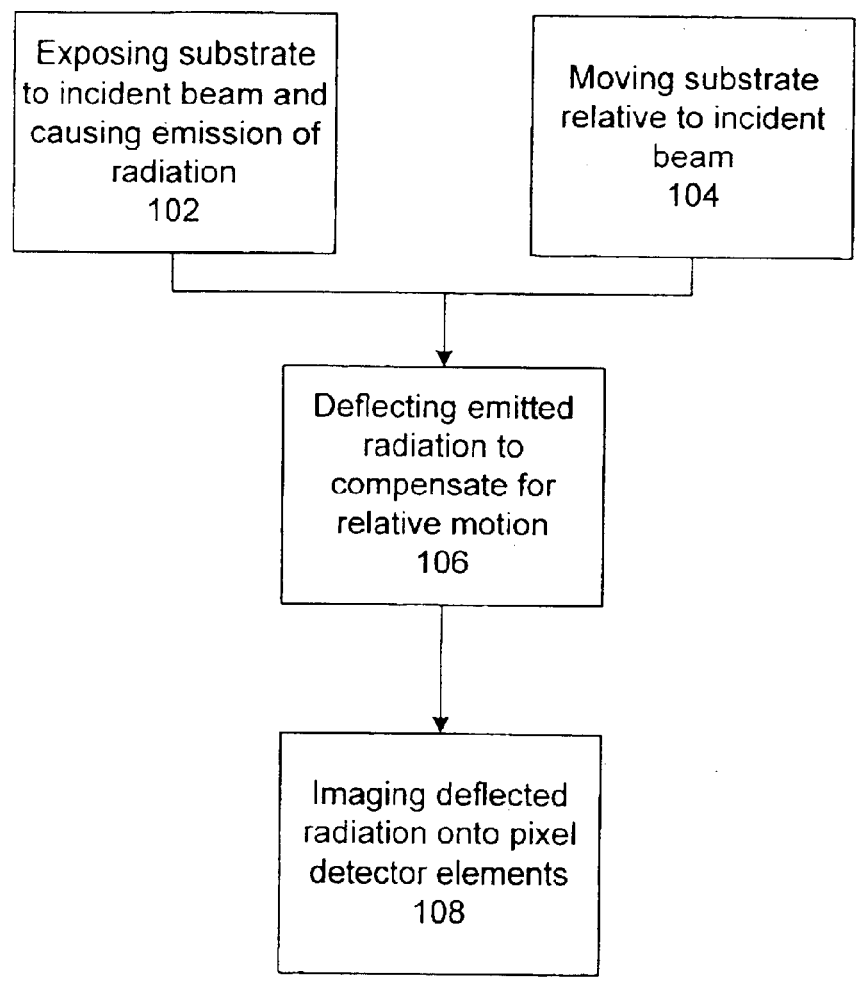
FIG. 1 is a flow chart depicting a method of inspecting a substrate in accordance with an embodiment of the invention.

FIG. 1 is a flow chart depicting a method of inspecting a substrate in accordance with an embodiment of the invention. At least a portion of the substrate is exposed 102 to an incident beam, which causes said portion to emit radiation. The emitted radiation may comprise, for example, emitted electrons. In one example, the emitted electrons may comprise secondary electrons. In another example, the emitted radiation may comprise incident electrons that are mirrored from said portion of the substrate.

During the exposure, the substrate is moved 104 relative to the incident beam. In one example, the substrate may be moved upon a stage. The stage may have some vibration motion in addition to a translation motion.

The emitted radiation is deflected 106 and imaged 108 onto at least one detector. The detector may comprise an array of pixel detector elements. In one example, the detector may comprise a time delay integration (TDI) detector. In another example, the detector may comprise one of a plurality of charge coupled device (CCD)-based detectors.

The deflection 106 compensates for the relative motion between incident beam and substrate and causes emitted radiation for each image pixel to accumulate at a corresponding detector element. Advantageously, this increases the resolution of the resulting image by preventing unnecessary blurring between pixels. Otherwise, the relative motion would cause a portion of the emitted radiation that should be detected by a certain detector element to be detected by one or more neighboring detector elements.

Figure 2:
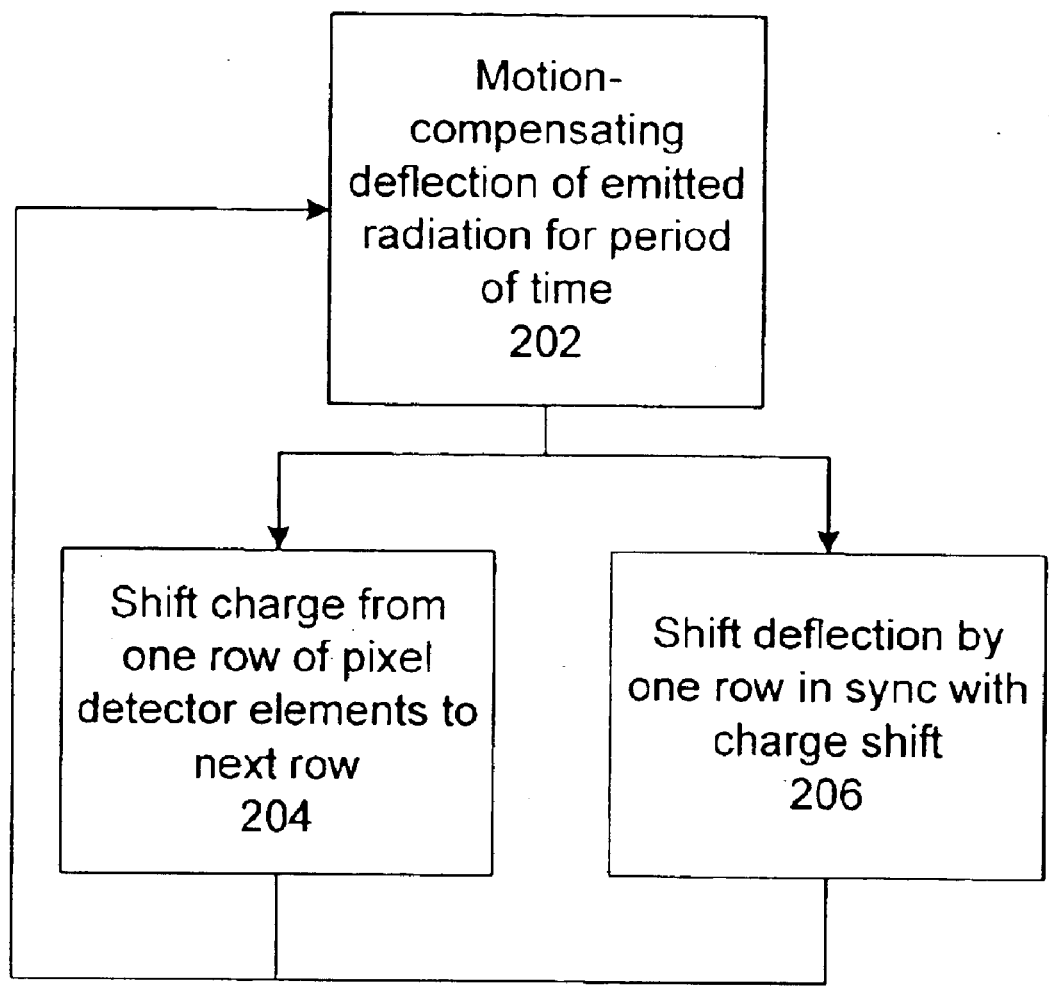
FIG. 2 is a flow chart depicting synchronization of the deflection of emitted radiation in accordance with an embodiment of the invention.

FIG. 2 is a flow chart depicting synchronization of the deflection of emitted radiation in accordance with an embodiment of the invention. The synchronization method shown in FIG. 2 is particularly applicable when a TDI detector is utilized.

As the substrate moves relative to the incident beam, motion-compensating deflection 202 of emitted radiation occurs for a period of time. In other words, the emitted radiation is deflected for a period of time to compensate for the relative motion between the incident beam and the substrate. The motion-compensating deflection 202 causes emitted radiation for the image pixels to accumulate at corresponding detector elements. The duration for the period of time depends on the speed of the relative motion and on the deflection capabilities and other parameters of the apparatus. The duration should be less than the maximum amount of time that the apparatus can deflect the emitted radiation so as to maintain a static correspondence between image pixels and detector elements.

After the period of time ends, a transition occurs. During the transition two things occur. The accumulated charges are shifted 204 from one row of detector elements to a next row of detector elements. This effectively shifts the image by one row on the array of detector elements. In addition, the deflection is shifted 206 by one row in synchronization with the charge shift. With both charge and deflection shifted by one row, the process loops back and the next period of time for the motion-compensating deflection 202 begins.

Figure 3:
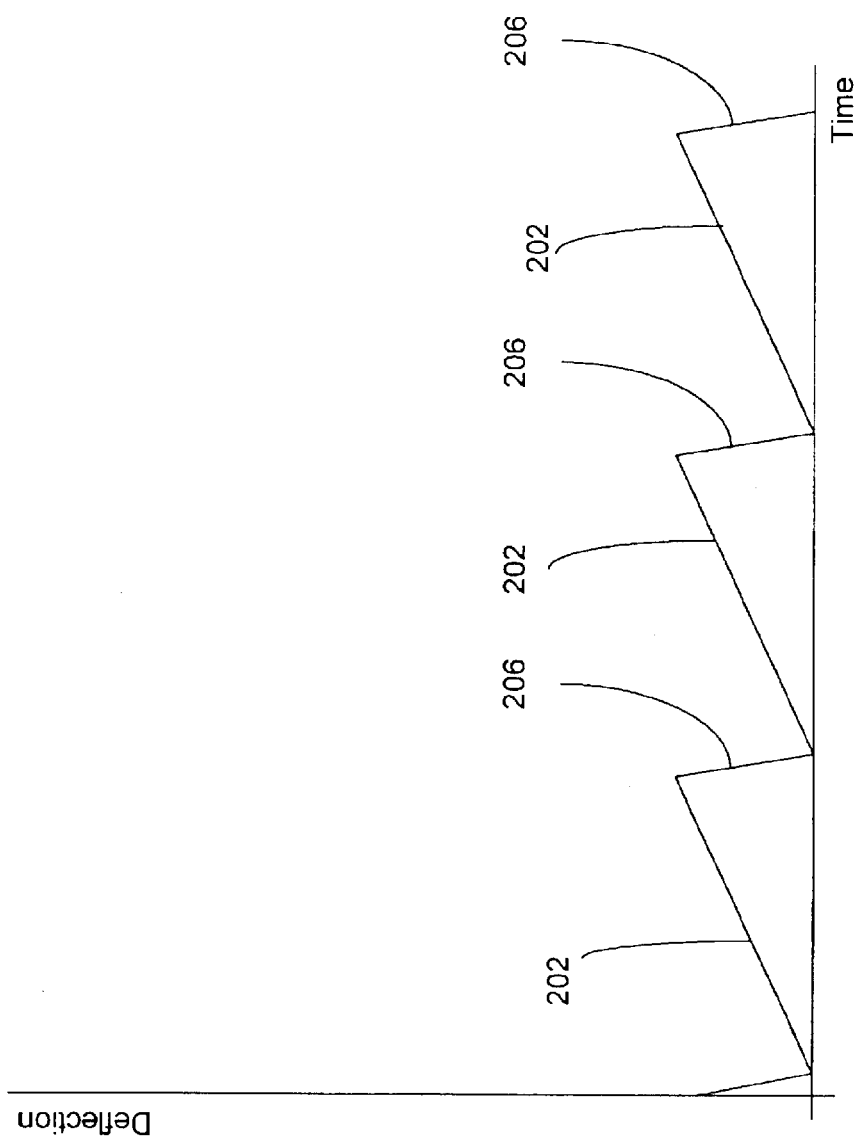
FIG. 3 is an example of a timing diagram for deflecting the emitted radiation in accordance with an embodiment of the invention.

FIG. 3 is an example of a timing diagram for deflecting the emitted radiation in accordance with an embodiment of the invention. The timing diagram of FIG. 3 is particularly applicable when a time delay integration (TDI) detector is utilized. The timing diagram plots a magnitude of the deflection of the emitted radiation versus time. A deflector control signal may follow, or be similar to, the sawtooth-shaped plot in the timing diagram.

The motion-compensating deflection 202 is shown in linear form in the example of FIG. 3. However, the motion-compensating deflection 202 may also have non-linear components or characteristics, depending on the particular configuration of the apparatus. At the end of each period of time, the deflection undergoes a transition during which the deflection is shifted 206 by the aforementioned one row of detector elements. After the shift 206 by one row, a following time period for the motion-compensating deflection 202 begins.

FIGS. 4A and 4B are illustrations of a correspondence of image pixels to detector elements before and after a transition in accordance with an embodiment of the invention. The illustrations of FIGS. 4A and 4B are particularly applicable to a TDI detector. As an image is scanned and charge is integrated with a TDI detector, accumulated charges are shifted from one row to the next in discrete increments. In other words, as the image pixels move from one row to the next, the accumulated charges are also transferred to the next row.

For reasons of simplification, the illustrations only depict a 5×5 array of detector elements. Of course, a practical detector would generally include a much larger array. In these figures, the detector elements are represented by the 5×5 grid of squares. The corresponding image pixels are represented by the symbols in the squares.

Prior to the transition (i.e. during one period of the motion compensating deflection 202), the correspondence is shown by FIG. 4A. Image pixels labeled D1 through D5 are shown to correspond to the first row (actually column in the illustration) of detector elements. Similarly, image pixels E1 through E5 correspond to the second row of detector elements, image pixels F1 through F5 correspond to the third row of detector elements, image pixels G1 through G5 correspond to the fourth row of detector elements, and image pixels H1 through H5 correspond to the fifth row of detector elements. In other words, the charge accumulating in the first row of detector elements correspond to image pixels D1 through D5. The charge accumulating in the second row of detector elements correspond to image pixels E1 through E5. And so on.

After the transition (i.e. during a next following period of the motion-compensating deflection 202), the correspondence is shown by FIG. 4B. As shown, the correspondence has been shifted 204 to the left by one row. As shown in FIG. 4B, image pixels labeled E1 through E5 are now shown to correspond to the first row (actually column in the illustration) of detector elements. Similarly, image pixels F1 through F5 correspond to the second row of detector elements, image pixels G1 through G5 correspond to the third row of detector elements, image pixels H1 through H5 correspond to the fourth row of detector elements, and image pixels 11 through 15 correspond to the fifth row of detector elements. In other words, the charge accumulations corresponding to the image pixels have been shifted 204 to the left by one row.

The accumulated charge for the image pixels D1 through D5 are shifted to a row of detector elements (not illustrated) to the left of the first row. The accumulated charge for the image pixels 11 through 15 came from a row of detector elements (not illustrated) to the right of the fifth row. Hence, in order for an array of detector elements to be practical, it should include a sufficient number of extra rows to allow the charge accumulations to be shifted until the integration for an image is complete.

Figure 5:
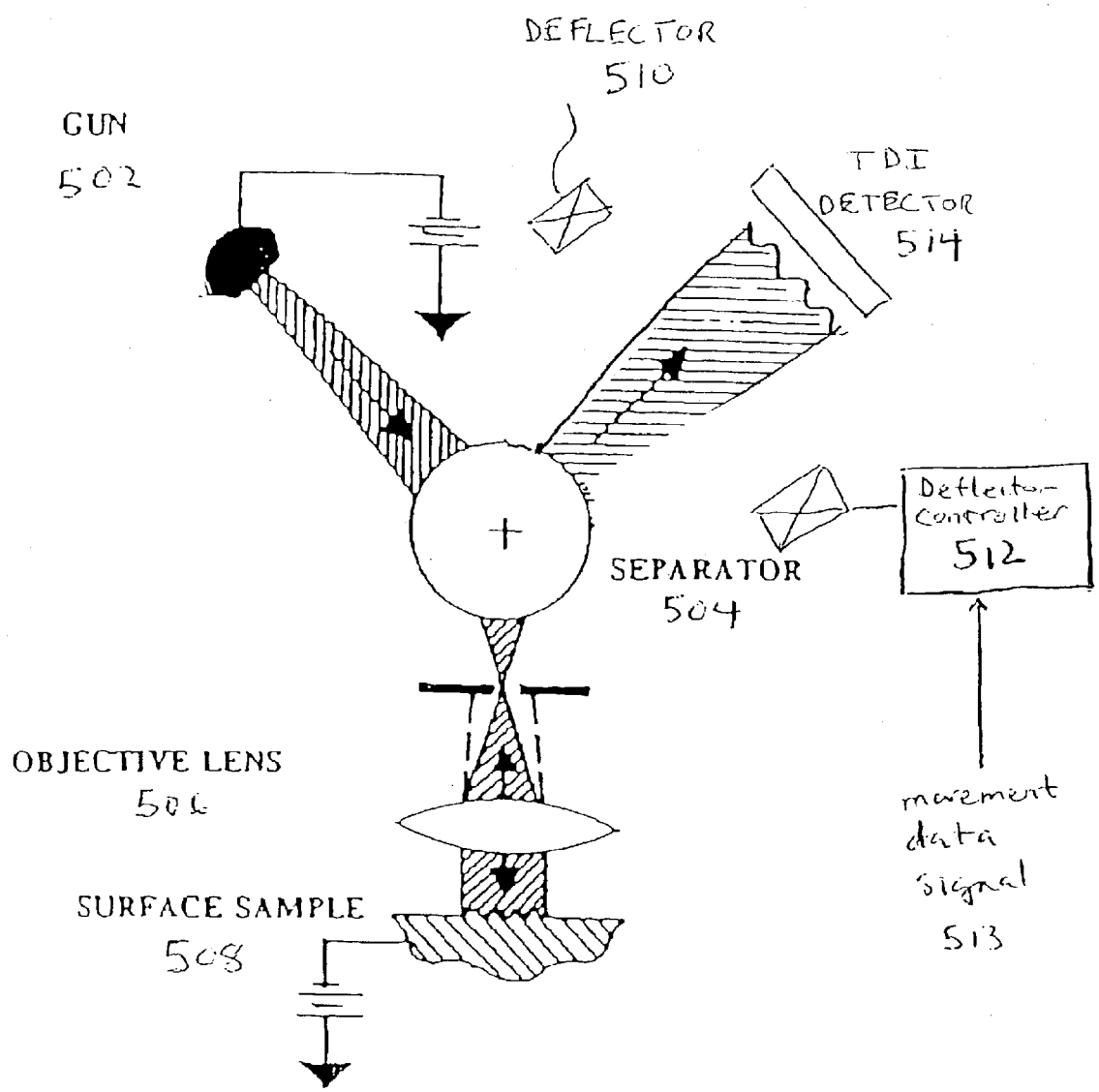
FIG. 5 is a schematic diagram of an apparatus for inspecting a substrate including a single detector in accordance with an embodiment of the invention.

FIG. 5 is a schematic diagram of an apparatus for inspecting a substrate including a single detector in accordance with an embodiment of the invention. The apparatus depicted comprises a direct (rather than scanned) electron beam instrument. The elements depicted include an electron gun 502, a beam separator 504, an objective lens 506, a surface of a sample substrate 508, a deflector 510, a deflector controller 512, and a detector 514.

The electron gun 502 supplies electrons that illuminate the sample or regions thereof. Advantageously, use of incident electrons allows observation of detail much smaller than a light optical microscope can resolve.

The beam separator 504 may comprise, for example, a magnetic prism. The beam separator 504 directs the incident electrons towards the substrate 508, and the objective lens 506 (which for example may comprise a magnetic lens) focuses the incident electrons onto a portion of the substrate 508. The incident electrons causes radiation in the form of secondary electrons or mirrored electrons to be emitted from the portion illuminated. The magnetic prism or other beam separator 504 deflects the emitted radiation in a direction that separates the emitted radiation from the incident beam.

A series of substrates 508 may be continuously moved under the incident beam in an inspection system or in similar such systems. In such systems, the substrate 508 under inspection may move relative to the incident beam. To compensate for the relative motion, the deflector 510 deflects the emitted radiation by a controlled amount prior to the emitted radiation being detected. The deflector 510 may comprise, for example, a magnetic or an electrostatic deflector.

A deflector controller 512 is coupled to the deflector 510. The deflector controller 512 transmits one or more control signals to the deflector 510 so as to control the magnitude (and, in certain embodiments, the direction) of the deflection. The deflector controller 512 may receive a movement data signal 513 that provides information on the motion of the substrate 508 relative to the incident beam. The movement data signal 513 may be derived, for example, using an interferometer to track the movement of the substrate.

The detector 514 receives the emitted radiation for imaging and generates image data therefrom. The detector 514 may comprise, for example, a TDI detector.

Figure 6:
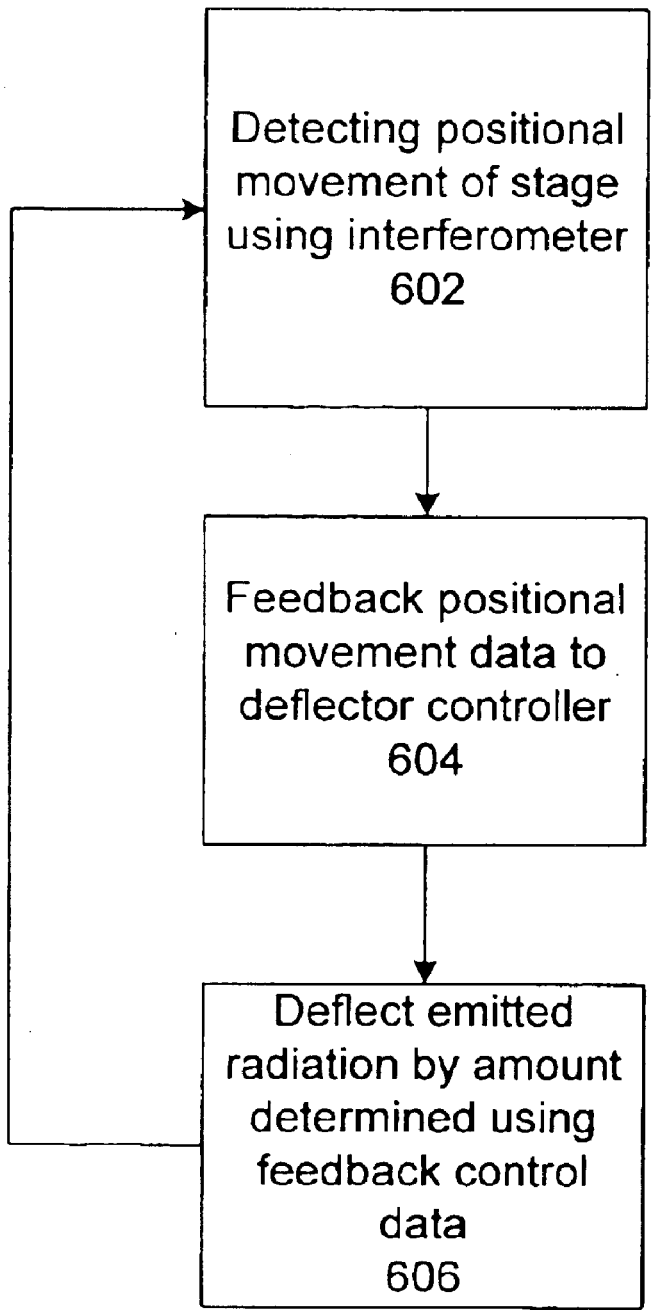
FIG. 6 is a flow chart depicting a feedback loop to control the motion-compensating deflection in accordance with an embodiment of the invention.

FIG. 6 is a flow chart depicting a feedback loop to control the motion-compensating deflection in accordance with an embodiment of the invention. The positional movement of the stage on which the substrate travels is tracked. For example, the tracking may be performed using an interferometer to detect 602 the positional movement of the stage. Data from the tracking of the positional movement is fed back 604 to the deflector controller. The emitted radiation is deflected 606 using the feedback control data to determine the magnitude (and in some embodiments, the direction) of the deflection. In embodiments where the incident beam also moves, data on the movement of the incident beam may also be fed into the deflector controller. In other embodiments, the incident beam may be stationary.

In some embodiments, there is vibration in the stage as it moves. The tracking data may include such vibrational movement such that the deflection 606 may also compensate for the stage vibration.

Figure 7:
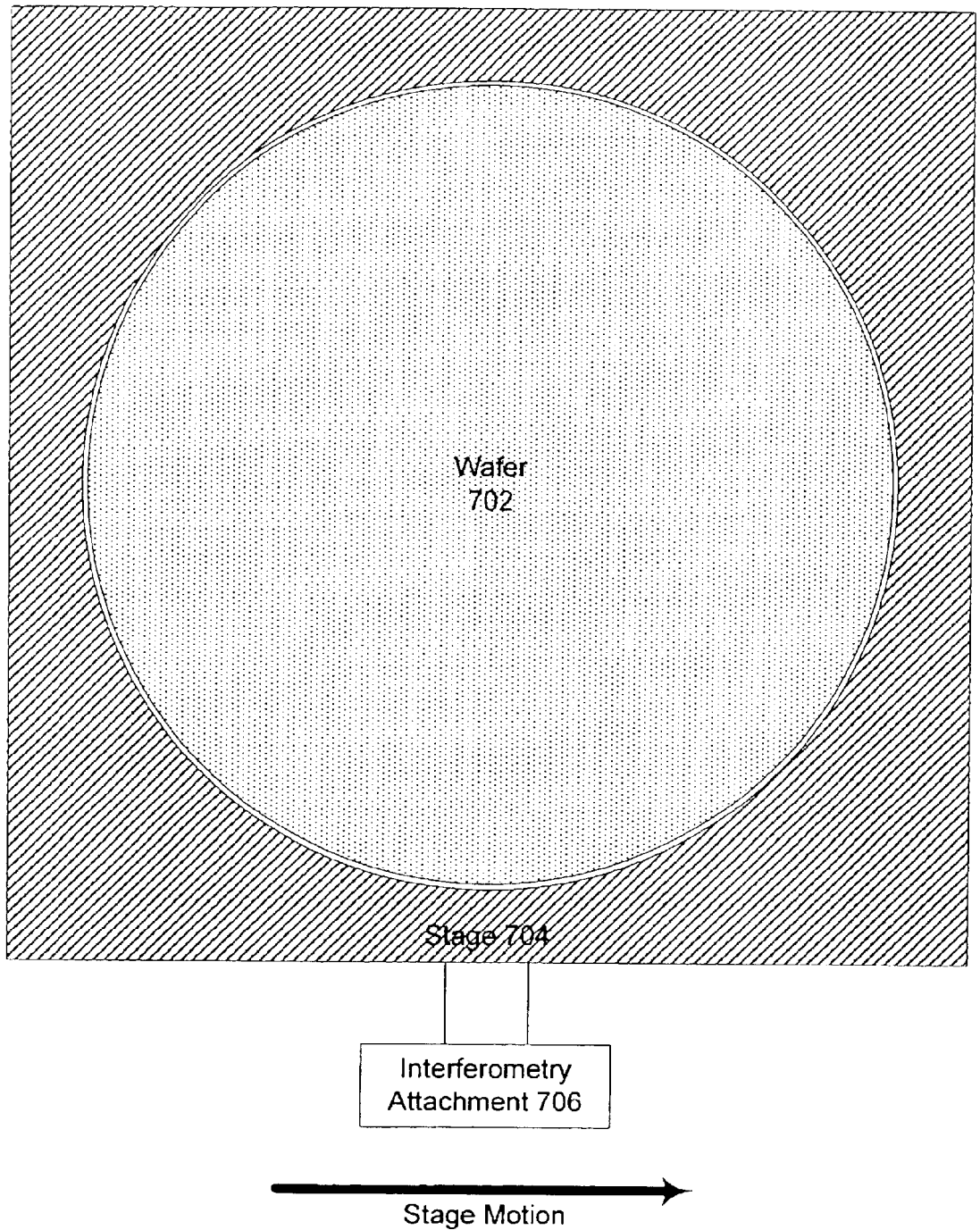
FIG. 7 is a schematic diagram of a stage including an attachment in accordance with an embodiment of the invention.

FIG. 7 is a schematic diagram of a stage including an attachment in accordance with an embodiment of the invention. The wafer 702 or other substrate is held by the stage 704. In order to inspect a series of substrates, such a stage may move laterally under the incident beam. An interferometry device 706 may be attached to the stage 704. One or more such interferometry attachments 706 may be utilized to track the stage motion. The attachment 706 may comprise, for example, a laser for the interferometry. In other examples, the attachment 706 may comprise a mirror or prism to redirect the laser beam used for the interferometry.

Figure 8:
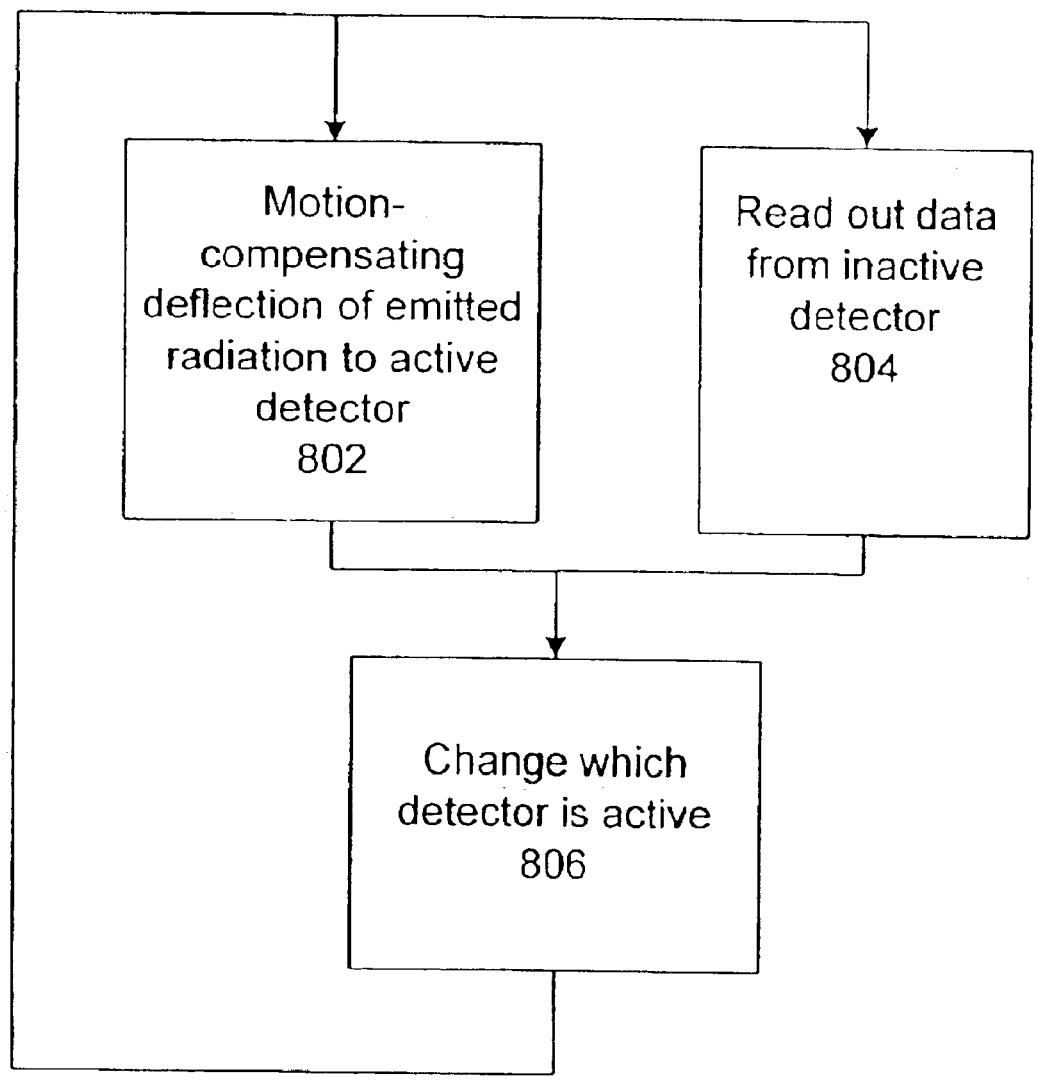
FIG. 8 is a flow chart depicting the use of multiple detectors in accordance with an embodiment of the invention.

FIG. 8 is a flow chart depicting the use of multiple detectors in accordance with an embodiment of the invention. The method of FIG. 8 is particularly applicable when a charge coupled device (CCD) detector is being utilized because there is typically a delay when data from the CCD array is being read out. The method should also be advantageous when utilized with other types of detectors with similar read-out delay characteristics.

As the substrate moves relative to the incident beam, motion-compensating deflection 802 of emitted radiation to an active detector occurs for a period of time. In other words, the emitted radiation is deflected 802 to the active detector for a period of time to compensate for the relative motion between the incident beam and the substrate. The motion-compensating deflection 802 causes emitted radiation for the image pixels to accumulate at corresponding detector elements. The duration for the period of time depends on the speed of the relative motion and on the deflection capabilities and other parameters of the apparatus. The duration should be less than the maximum amount of time that the apparatus can deflect the emitted radiation so as to maintain a static correspondence between image pixels and detector elements.

While the motion-compensating deflection 802 is occurring to the active detector, data is being read out 804 from a currently inactive detector (that previously was the active detector). This advantageously circumvents the read-out delay characteristic of the CCD array.

After the period of time ends, a transition occurs. Here, the transition to involves making the active detector to be inactive, and making an inactive detector (perhaps, but not necessarily the one from which data is being read out) to be the active detector. In other words, the active detector is changed 806 by shifting the deflection of the emitted radiation to a different one of the multiple detectors. Thereafter, the process loops back and the next period of time for the motion-compensating deflection 802 and data read-out 804 begins.

Figure 9:
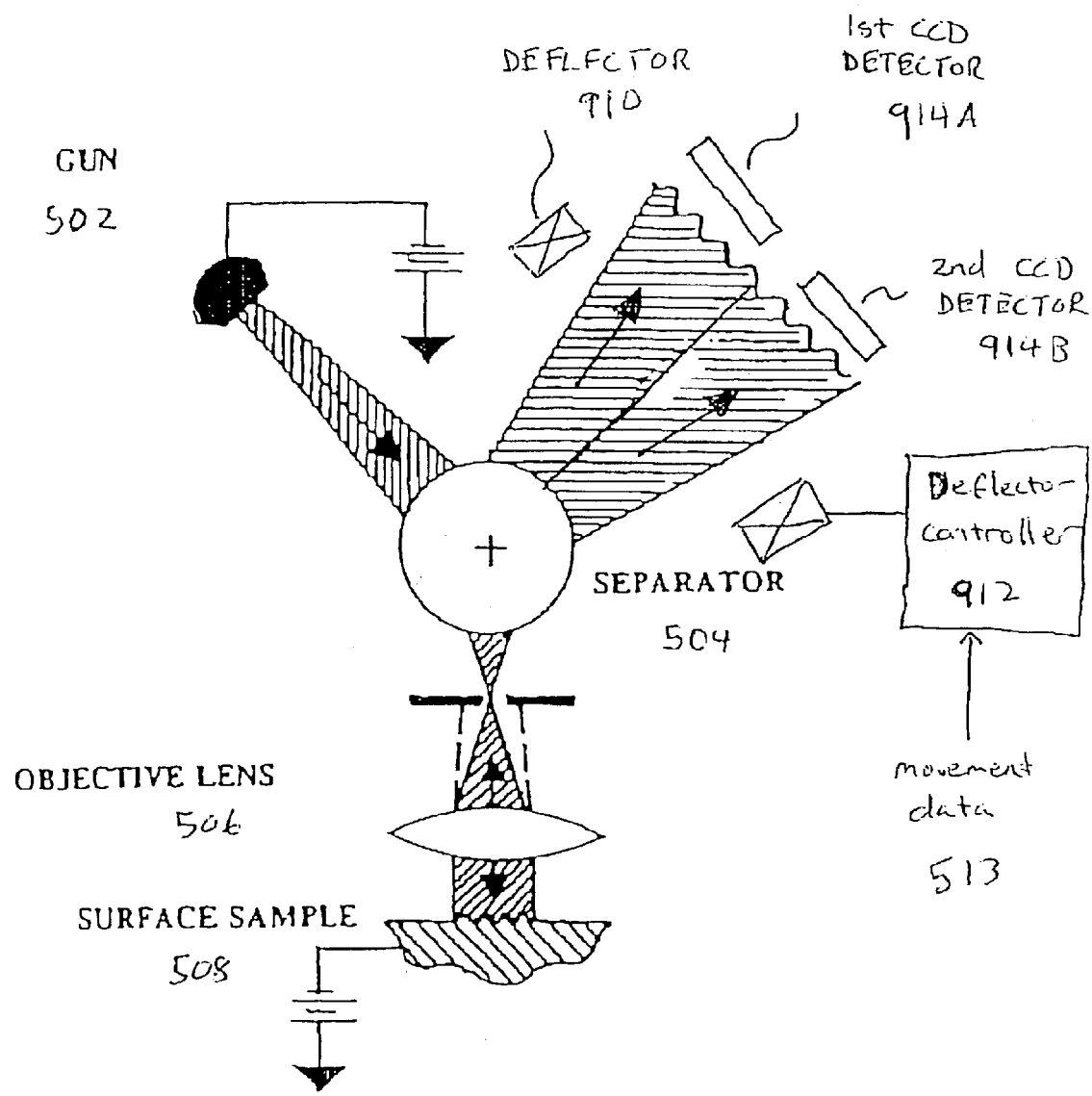
FIG. 9 is a schematic diagram of an apparatus for inspecting a substrate including, multiple detectors in accordance with an embodiment of the invention.

FIG. 9 is a schematic diagram of an apparatus for inspecting a substrate including multiple detectors in accordance with an embodiment of the invention. The apparatus depicted comprises a direct (rather than scanned) electron beam instrument. The elements depicted include an electron gun 502, a beam separator 504, an objective lens 506, a surface of a sample substrate 508, a deflector 910, a deflector controller 912, and two or more detectors 914. The primary differences between the apparatus of FIG. 5 and the apparatus of FIG. 9 comprises the deflector 910, the deflector controller 912, and the two or more detectors 914. The illustration of FIG. 9 shows two detectors 914A and 914B, but additional detectors may be utilized in other embodiments. These detectors may comprise CCD-based detectors or detectors with similar read-out delay characteristics.

Similar to the apparatus of FIG. 5, the electron gun 502 supplies electrons that illuminate the sample or regions thereof. The beam separator 504 may comprise, for example, a magnetic prism. The beam separator 504 directs the incident electrons towards the substrate 508, and the objective lens 506 (which for example may comprise a magnetic lens) focuses the incident electrons onto a portion of the substrate 508. The incident electrons causes radiation in the form of secondary electrons or mirrored electrons to be emitted from the portion illuminated. The magnetic prism or other beam separator 504 deflects the emitted radiation in a direction that separates the emitted radiation from the incident beam. A series of substrates 508 may be continuously moved under the incident beam in an inspection system or in similar such systems. In such systems, the substrate 508 under inspection may move relative to the incident beam.

The apparatus of FIG. 9 utilizes multiple detectors 914 to speed up the process, and so requires the imaging system to be configured differently than in FIG. 5. In particular, the deflector 910 should have a wider range of deflection capability so as to be able to deflect the emitted radiation from one detector to another detector. The deflector controller 912 should be configured so as to implement the method described above in relation to FIG. 8.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of inspecting a substrate, the method comprising:

exposing at least a portion of the substrate to an incident beam, the incident beam causing said portion to emit radiation;

moving the substrate relative to the incident beam during said exposure in a substantially continuous manner;

a first deflection of the emitted radiation to separate the emitted radiation from the incident beam;

imaging the emitted radiation onto at least one detector comprising an array of pixel detector elements;

shifting charge from one row of pixel detector elements to a next row in cycles synchronized with the relative motion between the substrate and the incident beam so as to provide a first compensation for said relative motion; and a second deflection of the emitted radiation that is synchronized with said relative motion within each said cycle so as to provide a second (more precise) compensation for said relative motion.

2. The method of claim 1, wherein the emitted radiation comprises electrons.

3. The method of claim 2, wherein said electrons are mirrored from said portion of the substrate.

4. The method of claim 2, wherein said electrons comprise secondary electrons.

5. The method of claim 1,
wherein a timing diagram of the second deflection has a substantially sawtooth form.

6. The method of claim 1,
wherein said substrate is moved upon a stage, and
wherein at least a portion of said second deflection compensates for stage vibration.

7. The method of claim 6, further comprising:
detecting movement in position of said stage using an interferometer; and
using data from said interferometer in a feedback loop to assist in controlling said second deflection.

8. The method of claim 1, wherein said radiation is imaged onto a plurality of detectors which each comprise an array of detector elements.

9. The method of claim 8, wherein said radiation is imaged onto a first of said arrays of detector elements while data is read out from a second of said arrays of detector elements.

10. The method of claim 9, wherein said first array of detector elements comprises a CCD array, and said second array of detector elements comprises a CCD array.

11. An apparatus for inspecting a substrate, the apparatus comprising:

an illumination system configured to expose at least a portion of the substrate to an incident beam which causes said portion to emit radiation;

a stage configured to hold said substrate and to move the substrate relative to the beam during said exposure of the substrate;

a beam separator for separating the emitted radiation from the incident radiation;

a multiple-pixel detector including an array of pixel detector elements configured to detect the emitted radiation;

an imaging system configured to image the emitted radiation onto the multi-pixel detector;

a deflector configured to deflect the emitted radiation in a controllable manner prior to said detection thereof; and a controller coupled to the deflector for controlling said deflection of the emitted radiation, wherein said multiple-pixel detector comprises a time delay integration (TDI) sensor, wherein the TDI sensor is configured to shift charge from one row of pixel detector elements to a next row in cycles synchronized with the relative motion between the substrate and the beam so as to provide a first compensation for said relative motion, and wherein said deflection is synchronized with the relative motion between the substrate and the beam within each said cycle so as to provide a second (more precise) compensation for said relative motion.

12. The apparatus of claim 11, wherein the incident beam comprises incident electrons, and wherein the emitted radiation comprises emitted electrons.

13. The apparatus of claim 12, wherein the deflector acts on the emitted electrons after separation from the incident electrons.

14. The apparatus of claim 11, wherein a timing diagram of the deflection has a substantially sawtooth form.

15. The apparatus of claim 11, further comprising:
a second multi-pixel detector including a second array of pixel detector elements configured to detect the emitted radiation,
wherein the imaging system is further configured to image the emitted radiation onto the second multi-pixel detector.

16. The apparatus of claim 15, wherein the arrays of pixel detector elements comprise CCD arrays, and wherein the emitted radiation is imaged onto one of the arrays of pixel detector elements while data is read out from another of the arrays of pixel detector elements.

17. The apparatus of claim 11, wherein at least a portion of said deflection compensates for vibration of the stage.

18. The apparatus of claim 17, further comprising:
an interferometer system for detecting movement in position of the stage; and
a feedback path from the interferometer system to the controller such that data from the interferometer system is used by the controller to assist in controlling said deflection.

19. A system for inspecting substrates, the system comprising:

means for exposing at least a portion of the substrate to an incident beam, the incident beam causing said portion to emit radiation;

means for moving the substrate relative to the incident beam during said exposure;

means to separate the emitted radiation from the incident beam;

means for deflecting the emitted radiation without deflecting the incident beam; and means for imaging the emitted radiation onto at least one detector, wherein said at least one detector comprises a time delay integration (TDI) sensor, wherein the TDI sensor is configured to shift charge from one row of pixel detector elements to a next row in cycles synchronized with the relative motion between the substrate and the incident beam so as to provide a first compensation for said relative motion, and wherein the means for deflecting is synchronized with the relative motion between the substrate and the incident beam within each said cycle so as to provide a second (more precise) compensation for said relative motion.

* * * * *